United States Patent [19]
Stetter et al.

[11] Patent Number: 5,226,309
[45] Date of Patent: Jul. 13, 1993

[54] HALOGENATED COMPOUNDS SENSOR

[75] Inventors: Joseph R. Stetter, Naperville; Zhuang Cao, Lisle, both of Ill.

[73] Assignee: Illinois Institute of Technology, Chicago, Ill.

[21] Appl. No.: 900,916

[22] Filed: Jun. 18, 1992

[51] Int. Cl.$^5$ .......................... H01C 7/00; G01N 27/04
[52] U.S. Cl. ...................................... 73/31.06; 338/34; 422/83; 422/98; 436/151
[58] Field of Search .......................... 73/31.06; 338/34; 422/83, 98; 436/147, 151

[56] References Cited
U.S. PATENT DOCUMENTS

| | | | |
|---|---|---|---|
| 3,751,968 | 8/1973 | Loh et al. | 73/31.05 |
| 3,865,550 | 2/1975 | Bott et al. | 73/31.06 X |
| 4,916,935 | 4/1990 | Novack et al. | 73/31.06 |

OTHER PUBLICATIONS

M. Shiratori, M. Katsura, and T. Tsuchiya, *Proceedings of the International Meeting on Chemical Sensors*, "Halogenated Hydrocarbon Gas Sensor", Fukuoka, Japan, T. Seiyama et al., editors (Elsevier, New York, 1983), pp. 119–124.

J. Unwin and P. T. Walsh, *Sensors and Actuators*, "An Exposure Monitor for Chlorinated Hydrocarbons Based on Conductometry Using Lead Phthalocyanine Films", Elsevier Sequoia 18, (1989) pp. 45–57.

J. R. Stetter, S. Zaromb, and M. W. Findlay, Jr., *Sensors and Actuators*, 6, "Monitoring of Electrochemically in Active Compounds by Amperometric Gas Sensors", Elsevier Sequoia, (1984) pp. 269–288.

Stetter, J. R., and Cao, Z., "Gas Sensor and Permeation Apparatus for the Determination of Chlorinated Hydrocarbons in Water", Anal. Chem., 62(2):182–185 (1990).

*Primary Examiner*—Robert J. Warden
*Assistant Examiner*—E. Leigh Dawson
*Attorney, Agent, or Firm*—Speckman, Pauley & Fejer

[57] ABSTRACT

A highly sensitive and selective sensor for the detection of halogenated compounds comprises a bead of sodium lanthanum fluoride silicate, having the molecular formula $NaLa_4(SiO_4)_3F$, in which are embedded two noble metal electrodes, preferably a straight platinum wire near the center and a helical platinum wire near the periphery of the bead. A current passing through the helical wire maintains the sensor temperature at about 550° C. by resistive heating. The electrical resistance between the two wires is deduced from measurements of the current passing through a fixed external resistor when a substantially constant voltage, preferably about 4 volts, is applied between the wires. A decrease in the measured resistance is an indication of the presence of a halogenated compound in the sample of air to which the bead is exposed. The sensor is preferably controlled by a microprocessor or microcomputer that also performs data processing. This system not only detects a halogenated compound of interest, but also measures its concentration.

20 Claims, 12 Drawing Sheets

HALOGENATED COMPOUNDS SENSOR

BACKGROUND OF THE INVENTION

This invention relates to a solid-state sensor for the detection of halogenated compounds, such as chloropentafluorobenzene, chlorobenzene, trichloroethylene, dichloromethane, chloroform, chloroethyl ethyl sulfide, dichlorodiethyl sulfide, bromobenzene, bromopropane, iodobenzene or iodopropane.

Many halogenated compounds, especially chlorinated hydrocarbons, are believed to be harmful to human health either through direct exposure (potential carcinogenicity) or indirectly through their adverse effect on the ultraviolet-absorbing stratospheric ozone layer. Sixteen chlorinated hydrocarbons are among the 25 organic compounds that were recently added by the Environmental Protection Agency to the list of chemicals that are to be regulated as toxic wastes under the Resource Conservation and Recovery Act. Rules have also been issued for a 50% reduction in the production and importation of chlorofluorocarbons by the year 1998.

To achieve the required controls, it will be necessary to resort to relatively inexpensive yet well-functioning halogenated compound monitors. It is an object of this invention to provide a sensor that is relatively inexpensive and portable and that can reliably detect various halogenated compounds.

Of the few sensors that have been developed for the detection of halogenated compounds, each has serious shortcomings. A chlorinated hydrocarbon gas sensor consisting of a ZnO-based semiconductor with vanadium, molybdenum and alumina catalysts was reported by M. Shiratori, M. Katsura, and T. Tsuchiya in the *Proceedings of the International Meeting on Chemical Sensors*, Fukuoka, Japan, T. Seiyama et al., editors (Elsevier, N.Y., 1983), pp. 119-124. Another sensitive sensor system for chlorinated hydrocarbons was reported by J. Unwin and P. T. Walsh in *Sensors and Actuators*, 18:45 (1989). This system decomposes the chlorinated compounds over a heated platinum coil and measures the changes in the electrical conductivity of a lead phthalocyanine film that is exposed to the decomposition products. Even earlier, Stetter et al. (*Sensors and Actuators*, 6:269-288 (1984)) reported the detection of such compounds by room-temperature electrochemical (amperometric) sensors following exposure to a heated noble-metal filament. The problem with all of these sensing systems is that they also respond to certain halogen-free compounds, such as methane, ethanol, benzene, hexane or nitrogen dioxide.

There are also gas chromatographic detectors for chlorinated hydrocarbons that are based on Hall conductivity or electron capture. These systems are complex, expensive, and sensitive to interferences.

It is therefore another object of this invention to provide a sensor that is relatively simple, inexpensive, and that can selectively detect halogenated compounds in the presence of potentially interfering substances.

A solid-state sensor, disclosed by J. C. Loh and C. Lu in U.S. Pat. No. 3,751,968, dated Aug. 14, 1973, was claimed to be capable of detecting dichlorodifluoromethane in a concentration as low as 20 ppbv (parts per billion by volume). The same sensor was also intended for the detection of other chlorofluorocarbons, as well as of sulfur hexafluoride, chloroform, and carbon tetrachloride. This sensor is formed of a glass-ceramic mixture of sodium or lithium silicate, lanthanum oxide, and lanthanum fluoride in a preferred molar ratio of $La_2O_3.(1-2)LaF_3.(3-4)Na_2SiO_3$. The preparation of this sensor involves the formation of a surface depletion layer through application of a "biasing D.C. voltage of 1-10 volts" at a temperature above 550° C., preferably 600° C., for approximately 24-48 hours. No information is disclosed in the patent about the performance of this sensor. However, in view of the wide range of preferred molar ratios, one would expect the performance to vary widely from unit to unit.

It is therefore still another object of this invention to provide a sensor that can be prepared in a relatively short time, preferably in not more than about eight hours, and that has well-defined and reproducible performance characteristics.

Other objects of the invention will become obvious to professionals in various fields, such as industrial hygiene or pollution monitoring, following perusal of the complete specification.

SUMMARY OF THE INVENTION

Briefly, the sensor consists of a bead of sodium lanthanum fluoride silicate, having the molecular formula $NaLa_4(SiO_4)_3F$., in which are embedded two noble metal electrodes, preferably a straight platinum wire near the center and a helical platinum wire near the periphery of the bead. A current passing through the helical wire maintains the sensor temperature at about 550° C. by resistive heating. The electrical resistance between the two wires is deduced from measurements of the current passing through a fixed external resistor when a substantially constant voltage, preferably about 4 volts, is applied between the wires. A decrease in the measured resistance is an indication of the presence of a halogenated compound in the sample of air to which the bead is exposed. The sensor is preferably controlled by a microprocessor or microcomputer that also performs data processing. This system not only detects a halogenated compound of interest, but also measures its concentration.

BRIEF DESCRIPTION OF THE DRAWINGS

The invention is best explained with reference to the drawings, in which.

DESCRIPTION OF THE PREFERRED EMBODIMENT

Ancillary Components

Figure 1:
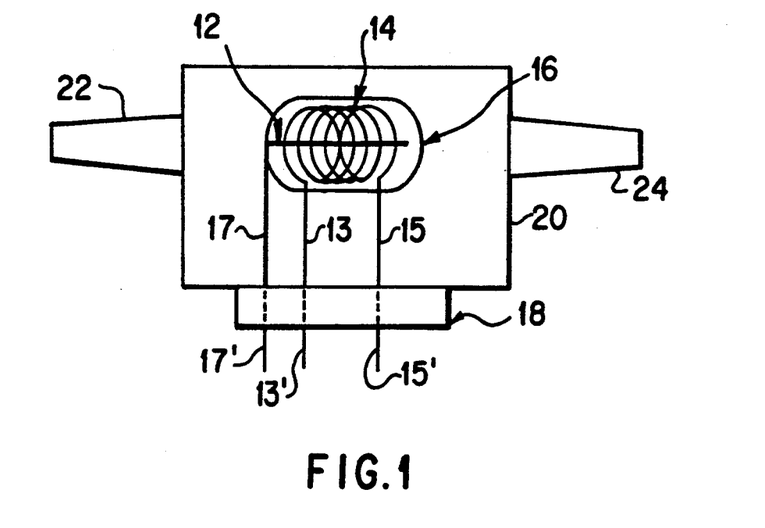
FIG. 1 is a schematic diagram of the main components of the sensor.

As shown in the schematic diagram of FIG. 1, the sensor of this invention comprises a platinum wire 12 surrounded by a platinum coil 14, both embedded in a bead 16 that is composed mainly of $NaLa_4(SiO_4)_3F$. The two ends 13 and 15 of coil 14 and one end 17 of wire 12 are connected to pins 13', 15', and 17', respectively, of a three-pin miniature transistor socket 18. Bead 16 is enclosed within a chamber 20 comprising an air inlet 22 and an air outlet 24. Chamber 20 is preferably made of an electrically conductive material, such as aluminum, to provide electrical shielding, and should be covered by a thermally insulating material to provide thermal shielding.

To form bead 16, coil 14 is first prepared by winding six turns of a platinum wire, preferably about 0.1 mm in diameter, around a 1.5-mm-diameter rod, so as to produce a coil length of about 2.5 mm, sliding the coil off the rod, and mounting the two ends of the coil 13 and 15 onto socket 18. Next, lanthanum oxide ($La_2O_3$) and lanthanum fluoride ($LaF_3$) powders are mixed with an aqueous solution of sodium silicate ($Na_2SiO_3$) to form a paste. The three components of the paste are preferably in a molar ratio corresponding to the chemical formula $La_2O_3.2LaF_3.3Na_2SiO_3$. One end portion of wire 12 is then coated with the paste and dried by heating. The coated wire is fitted axially into the coil, and additional paste is applied so as to fully cover the coil and fill the space between the coil and the wire. The bead is finally formed by gradual raising of the temperature followed by sintering at about 800° C. for 3–8 hours.

To determine the composition of the bead after sintering at 800° C., a pair of x-ray diffraction (XRD) spectra were obtained using a Philips Model XRG 3100 x-ray diffractometer. Two samples were prepared from : (1) a mixture of lanthanum oxide and lanthanum fluoride powders without the sodium silicate; (2) a sintered sensor bead (lanthanum oxide and lanthanum fluoride with the sodium silicate after sintering). The XRD spectra showed a big difference between the two samples. The spectrum of the powder mixture had the diffraction patterns of $LaF_3$ and $La_2O_3$, but this diffraction pattern was not found in the spectrum of the sintered bead, which was consistent with the powder diffraction patterns of $NaLa_4(SiO_4)_3F$ and $NaF$. This leads to the following proposed chemical reaction of the sensor starting materials during sintering:

(1).

Figure 2:
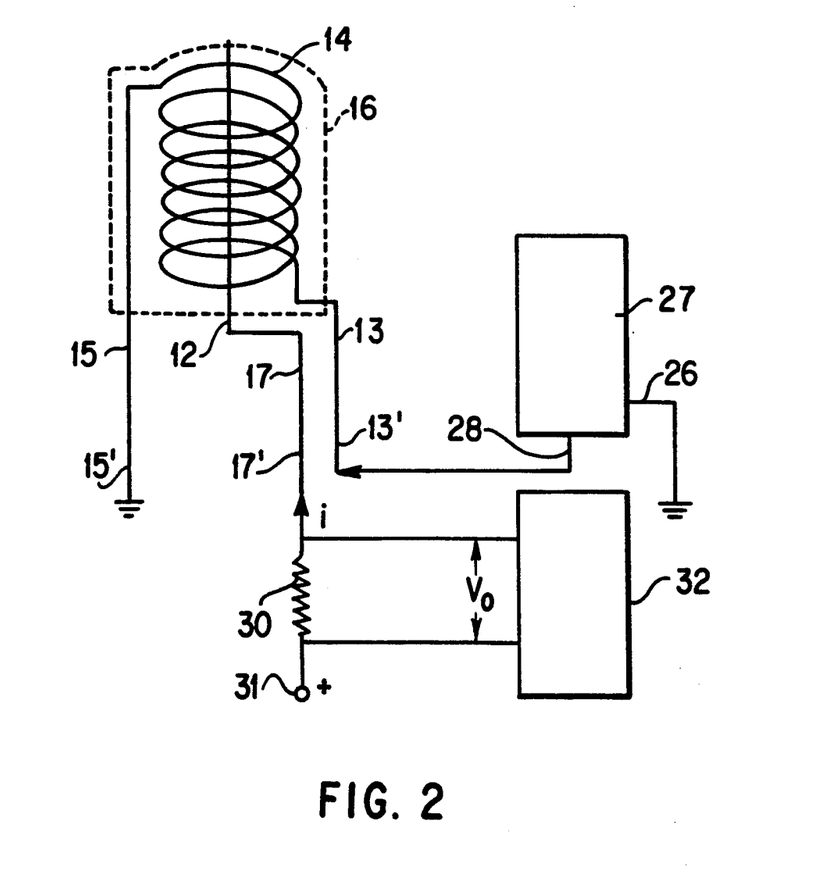
FIG. 2 shows the basic electrical circuit that is required for the operation of the sensor.

To be operational, the sensor must form part of the electric circuit of FIG. 2, in which:

pin 15' is connected through the ground to one output terminal 26 of a heater power supply 27 and to the negative terminal of a battery (not shown);

pin 13' is connected to a second output terminal 28 of power supply 27; and pin 17' is connected to one end of a resistor 30, which is connected at its other end to the positive terminal 31 of the same battery.

Figure 3:
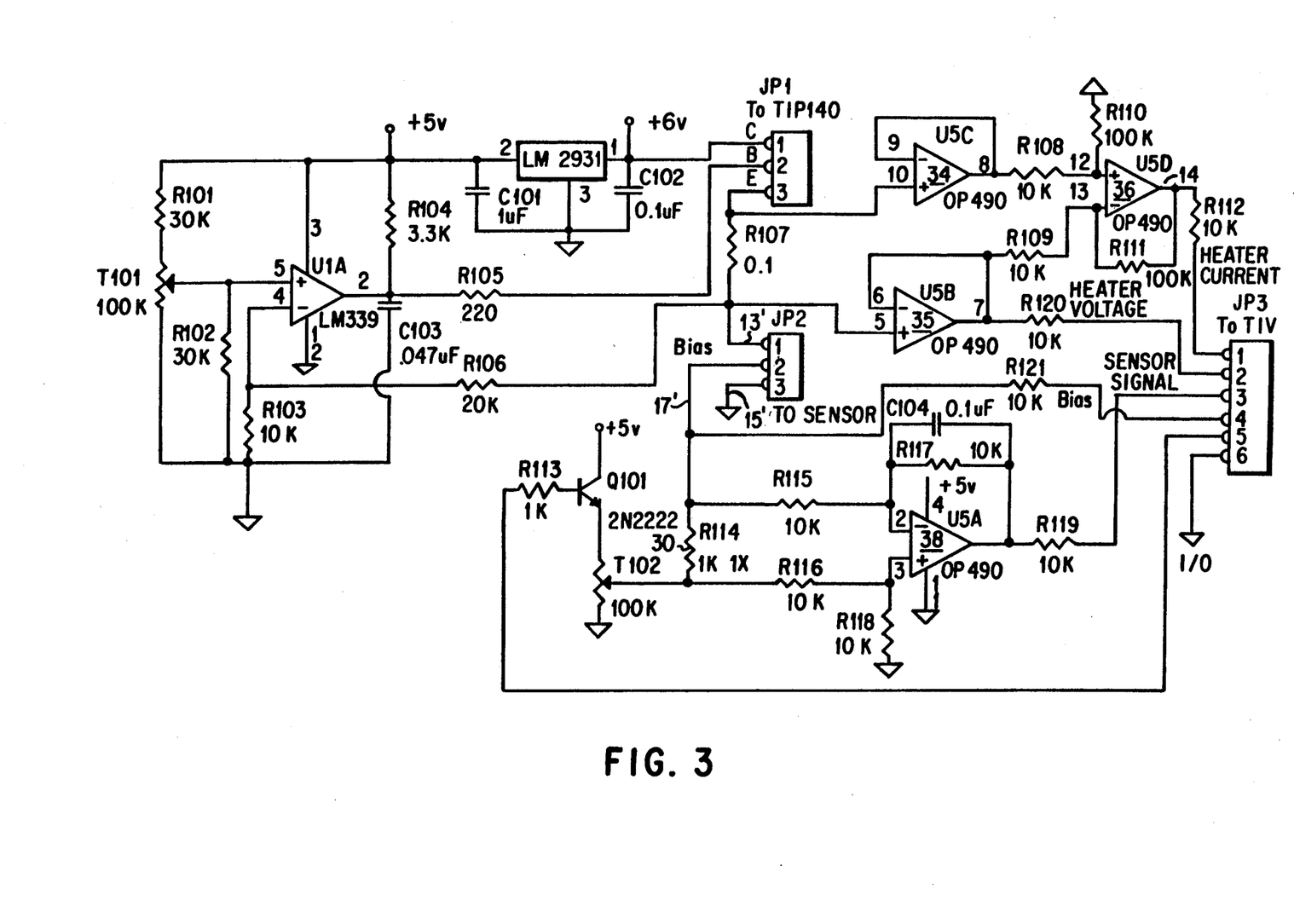
FIG. 3 is a more detailed circuit diagram including illustrative examples of the components 27 and 32 of the circuit of FIG. 2.

The current i that flows through resistor 30, wire 12, bead 16, and coil 14 is then determined by measuring the voltage drop $V_o$ across resistor 30 using an appropriate device 32, which may be a simple voltmeter, a recorder or a signal amplifier and microprocessor circuit, such as that included in FIG. 3.

The circuit of the heater power supply 27 is also included in FIG. 3. The sensor temperature is raised to a preferred value, usually 550° C., by resistive heating of coil 14. The current through coil 14 is regulated to maintain a constant sensor temperature. This yields a sensor output that is not affected by line-voltage variations, shortens the warm-up time of cold sensors, and minimizes sensor output drift.

Making use of the known temperature coefficient of the electrical resistivity of platinum, the temperature of coil 14, and hence of the sensor bead 16, can be controlled by a comparator circuit comprising a low-power-drain quad comparator LM 339, a heater temperature-adjusting potentiometer T101 with two fixed resistors R101 and R102, a pull-up resistor R104, a buffer capacitor C103, a current-limiting resistor R105, an N-P-N Darlington power transistor TIP 140, and a feedback loop with three fixed resistors R103 R106 and R107. The potential at pin 5 of quad comparator LM 339 is set by the adjustable potentiometer T101 and is limited by the two fixed resistors R101 and R102. When the sensor temperature is too low, so is the coil resistance, and the potential at pin 4 of the comparator LM 339 is lower than the potential setting at pin 5. The output at pin 2 of the comparator LM 339 is then high. The power transistor TIP 140 then supplies a high current to the sensor heater and raises the sensor temperature. When the sensor temperature is too high, so is the coil resistance, which causes the potential at pin 4 of the comparator LM 339 to be higher than the potential setting at pin 5. The output at pin 2 of the comparator LM 339 is then reduced, and the heater current is shut-off. This feedback function maintains a constant sensor temperature and also shortens the warm-up time of a cold sensor. A voltage regulator LM 2931 is used to convert 6 volts DC to 5 volts DC for the power supply of the comparator LM 339 and the voltage input of potentiometer T101.

The temperature of the sensor is monitored by recording the current and voltage across coil 14 with a Tattletale IV microprocessor (not shown) made by Onset Computer Corp., North Falmouth, Mass. Since this microprocessor only records a voltage signal, a current-to-voltage converter is used to transform the heater current into a voltage signal. This converter circuit is formed by three high-performance micropower quad operational amplifiers (OP 490) 34, 35, and 36.

This sensor bias voltage is preset by a transistor Q101. The bias voltage is adjustable with a potentiometer T102. The voltage across the fixed resistor 30 (R114) yields a measure of the current changes that occur when the sensor is exposed to halogenated compounds. Since the actual current between the two electrodes 12 and 14 of the sensor is very low, a fourth quad precision operational amplifier (OP 490) 38 is used to convert the current into an amplified voltage signal. This amplifier circuit can be interfaced with a computer for data logging and processing.

Figure 4:
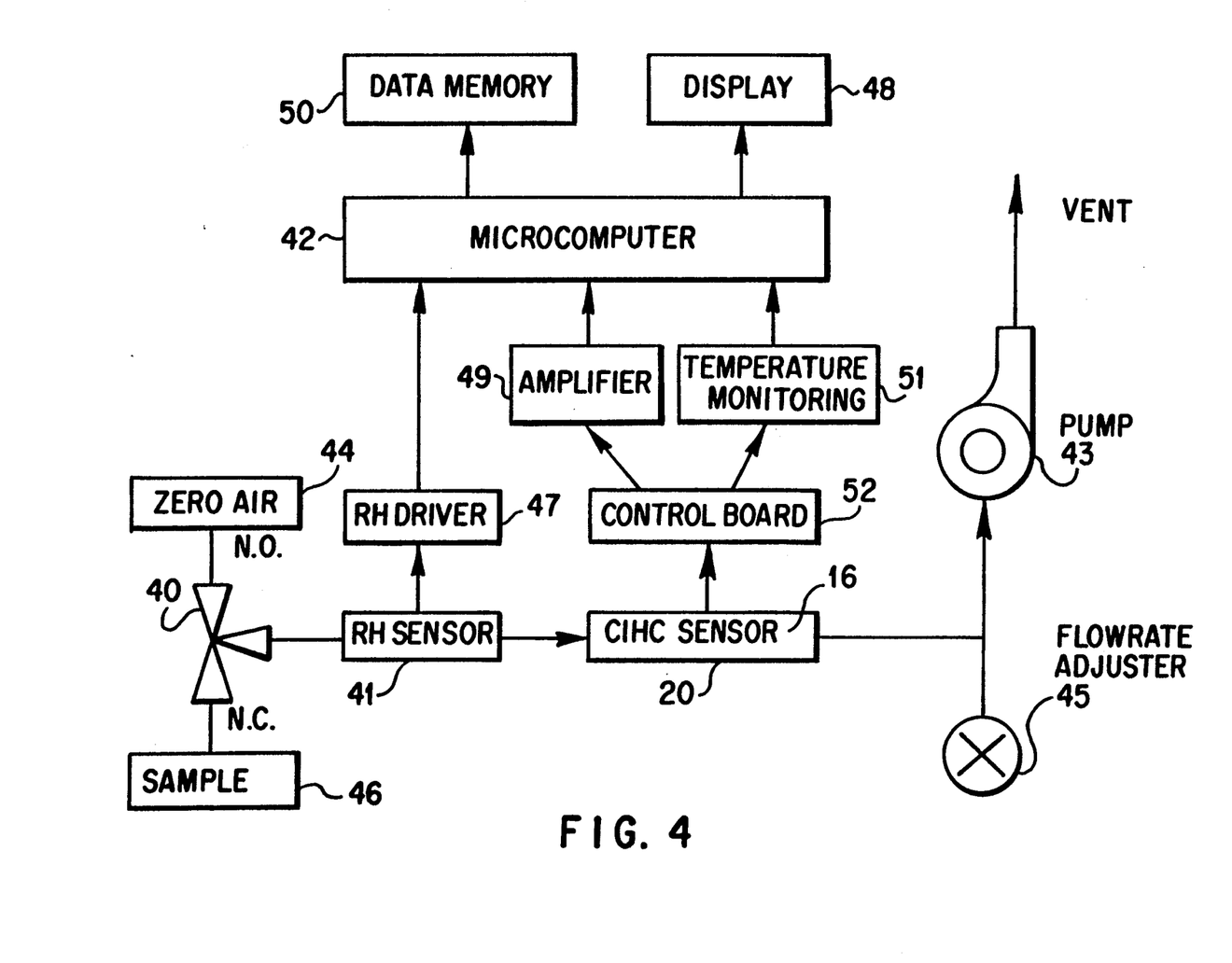
FIG. 4 is a block diagram of a complete monitoring system incorporating the sensor and circuitry of FIGS. 1 through 3.

A schematic diagram of a complete system for monitoring halogenated hydrocarbon vapors is shown in FIG. 4. An electric solenoid valve 40 controlled by a microcomputer 42 opens one of two inlets 44 and 46 which admit either pure air, also referred to as "zero air," or the gaseous sample into a flow system that includes a relative humidity (RH) sensor 41, the sensor chamber 20 (with the sensor bead 16), and an air pump 43. By switching valve 40, it is possible to rapidly change the flow over the sensor bead 16 from that of clean air to that of sampled air. The flow is preferably maintained constant at about 170 mL/minute by means of a flow adjuster 45. A measurement cycle preferably includes sample exposure for 5 min followed by clean air exposure for 5-10 min. The signals from the RH sensor are transferred by an instrument circuit 47, also referred to as "RH driver," to the microcomputer 42. Also transferred to the microcomputer by the amplifier 49 and temperature monitor 51—both of which form part of the circuit of FIG. 3—are the changes in the conductance of bead 16, also referred to as "sensor signals," as well as the temperature of coil 14. The microcomputer 42 serves to record the sensor signals, to control valve 40 and a display 48, and to store the collected data in a memory 50. A control board 52 may be used to adjust the sensor temperature and other test conditions, such as the operation of valve 40 or the flow rate.

Figure 5:
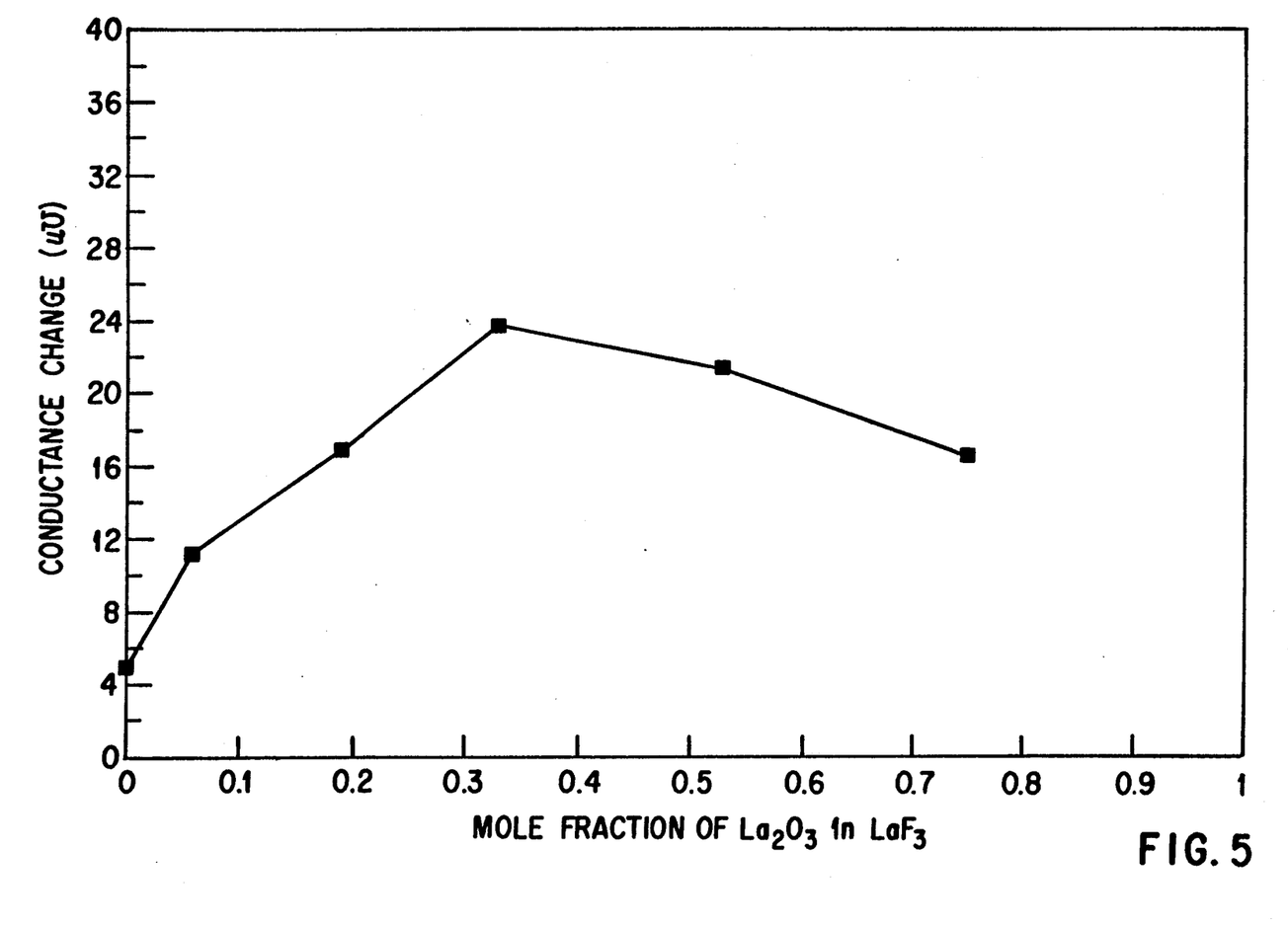
FIG. 5 is a plot of sensor responses versus the mole fraction of $La_2O_3$ in the powder mixture that is used to prepare the sensor bead of FIG. 1.

Several sensors prepared as described in the above explanation of FIG. 1, but with different mole ratios of lanthanum oxide to lanthanum fluoride, were each exposed to 50 ppmv of dichloromethane in air. The dependence of the sensor signal on the mole fraction of lanthanum oxide in lanthanum fluoride is shown in FIG. 5. It can be seen that the optimum ratio yielding the strongest signal is one mole of lanthanum oxide to two moles of lanthanum fluoride. This is consistent with the mole ratios of equation 1 that were deduced from XRD measurements. Both sets of results support the conclusion that an essential component of the sensor bead is sodium lanthanum fluoride silicate, $NaLa_4(SiO_4)_3F$, with or without sodium fluoride.

Preferred Operational Parameters

Operating Temperature

Figure 6:
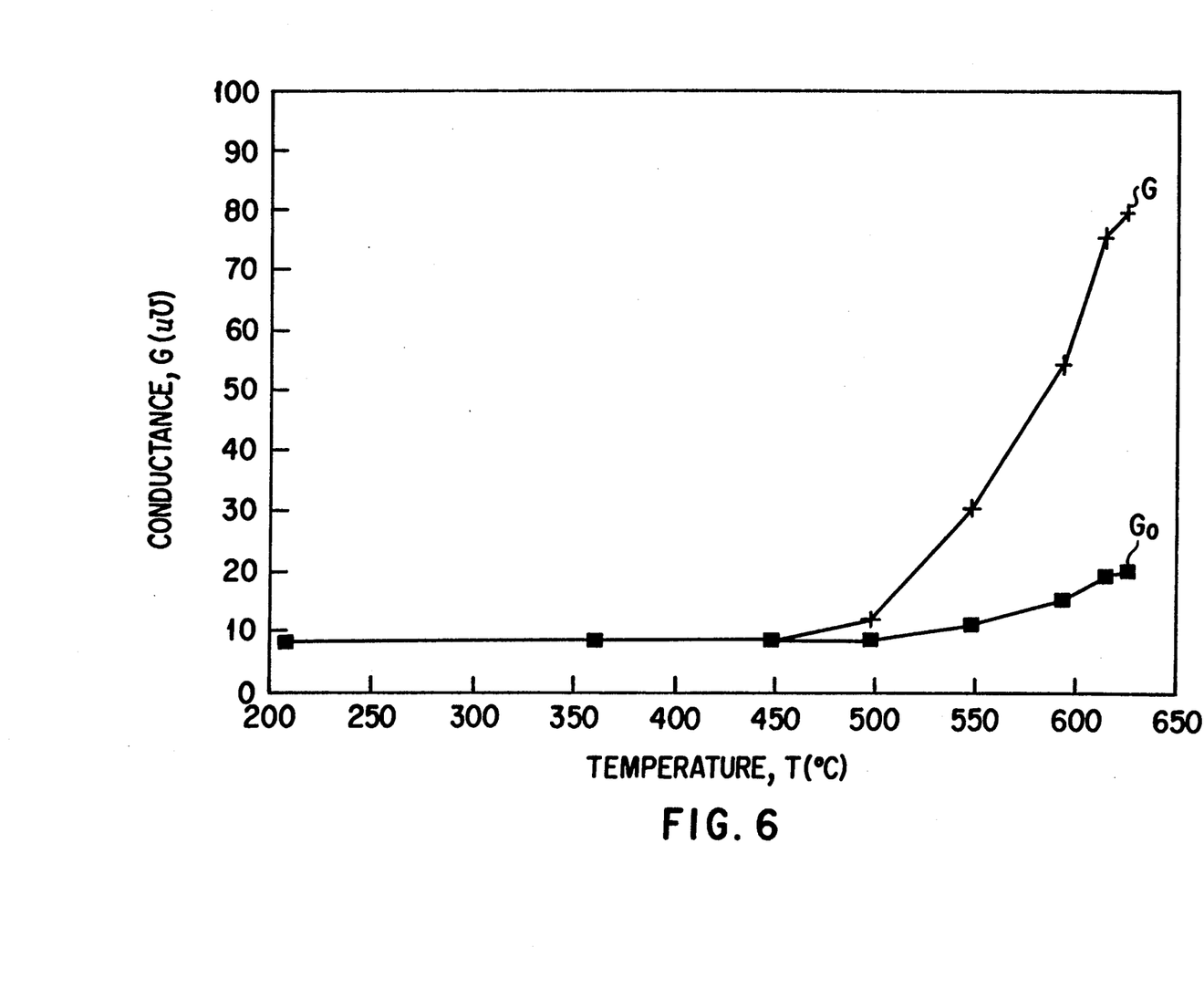
FIG. 6 shows the temperature dependence of the sensor response to 250 ppmv (parts per million by volume) of $CHCl_3$.

The sensitivity of the sensor is highly dependent upon the voltage of the heater that controls the temperature of the sensor. The graph of sensor signals versus temperature at a constant concentration of 250 ppmv of chloroform in air is plotted in FIG. 6. Here G is the conductance when the sensor is exposed to chloroform, while $G_o$ is the conductance in pure air. There is no sensor signal below 450° C. The signal increases steeply with temperature up to 620° C., above which temperature the rate of increase is slower. To prolong the lifetime of the sensor, it is preferable to operate the sensor at a temperature of 550° C.

Flow Rate

At a high flow rate, the sensor signal decreases with the flow rate. This effect may be due to a removal of heat from bead 16 by the flowing air that is not adequately compensated for by the heating of coil 14. Table 1 shows the dependence of the sensor signal on flow rate. Although a lower flow rate yields a higher signal, it also tends to slow down the sensor response. Therefore, a flow rate of about 170 mL/min was chosen for the sensor geometry of FIG. 1.

TABLE 1

| Relationship between Sensor Signal and Flow Rate | | | | | | | |
|---|---|---|---|---|---|---|---|
| Flow rate (cm$^3$/min) | 110 | 150 | 175 | 200 | 310 | 360 | 516 |
| Conductance, G ($10^{-6}$ mho) | 14.8 | 11.5 | 9.63 | 8.12 | 3.76 | 2.96 | 1.16 |

Bias Voltage

Figure 7:
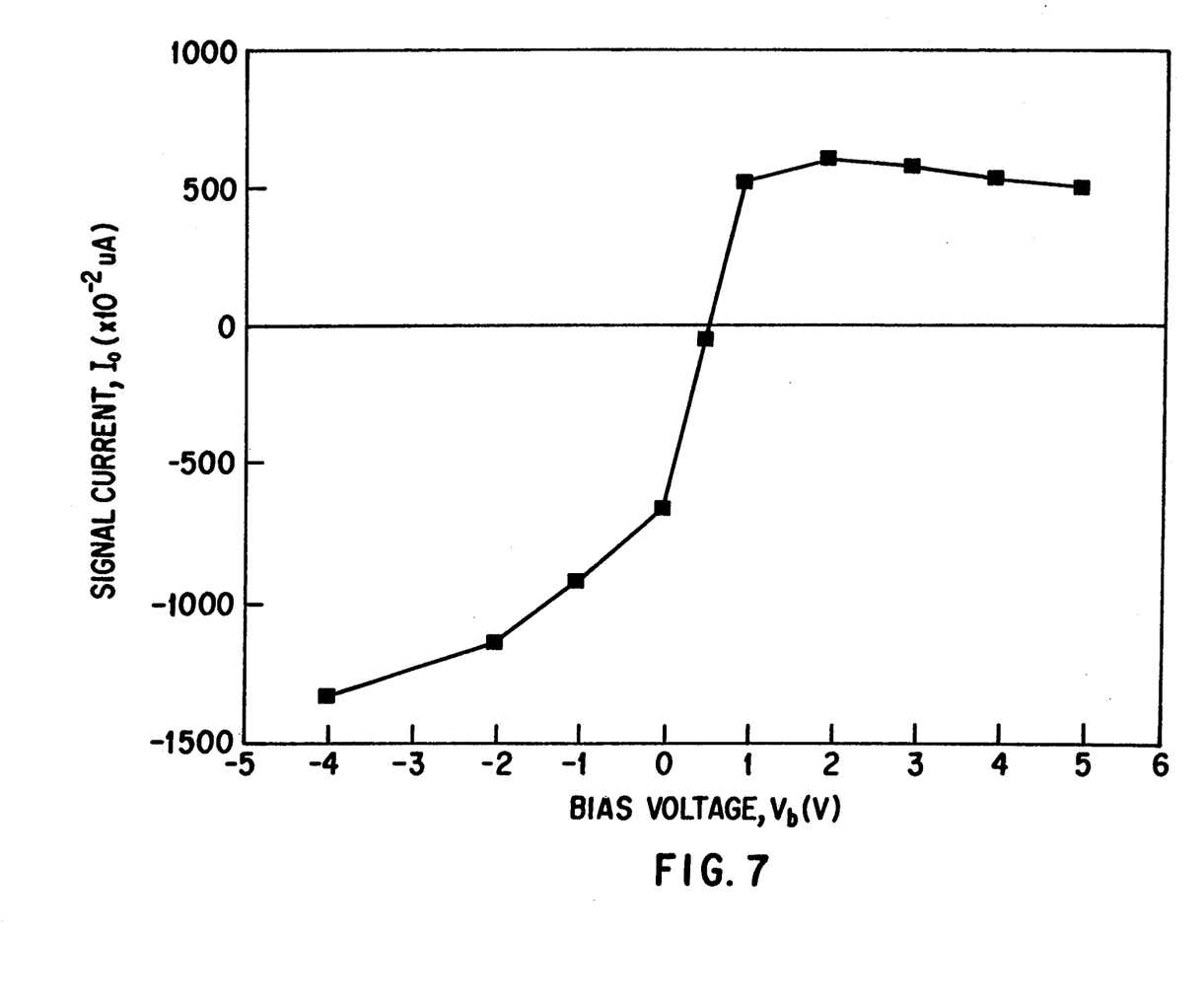
FIG. 7 shows the effect of bias voltage on the response of the sensor to 100 ppmv of 1,1,2-trichloroethylene.

The effect of the sensor bias voltage was determined by exposing the sensor to 100 ppmv of 1,1,2-trichloroethylene vapor in air and measuring the sensor signal at bias voltages between −4 volts and +5 volts. The dependence of the sensor signal (change in current) on the bias voltage is shown in FIG. 7. When the bias voltage changes from negative to about +1 volt, the direction of the sensor current changes too. This current-voltage curve indicates that the sensor bead behaves as a two-terminal component, but not as a real resistor because the current does not usually increase linearly with the applied voltage. Therefore, the sensor conductance or resistance that is measured by the circuit of FIG. 3 represents an "effective conductance" or "effective resistance" that is valid only for a given applied bias.

Sensor Characteristics

Sensitivity and Selectivity

Figure 8:
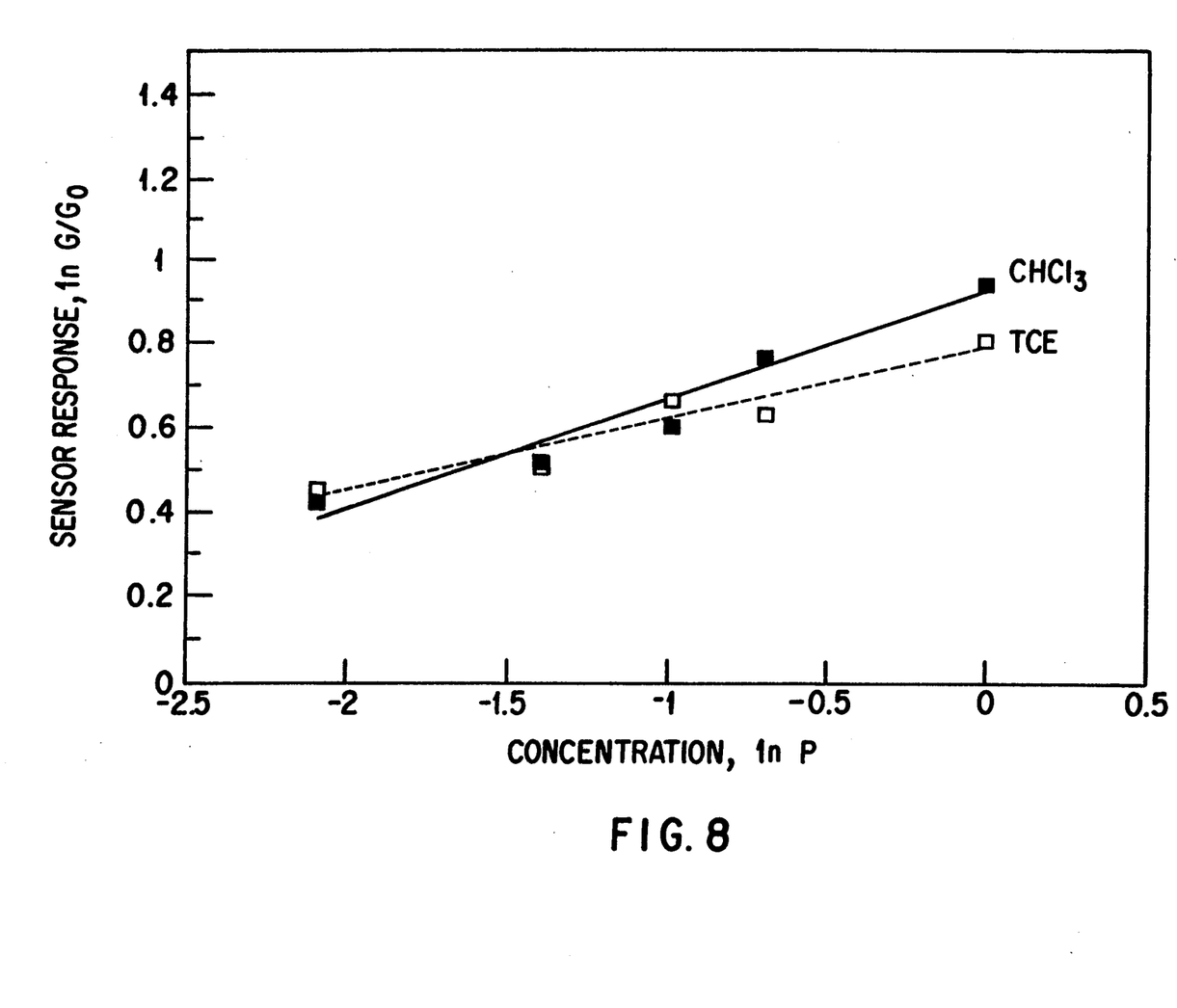
FIG. 8 shows the variations with concentration of the sensor responses to 1,1,1-trichloroethane in the concentration range of 0.125-1 ppmv.

The sensor was exposed to two chlorinated hydrocarbon vapors, chloroform and 1,1,1-trichloroethane. Responses at various vapor concentrations (0.125-1 ppmv) were recorded using an amplifier gain of 100 to boost the signal. The linear log-log relationship of the relative conductance, $G/G_o$, and the gas concentration, P (in ppmv units), of chlorinated hydrocarbon vapors is shown in FIG. 8. Other halogenated compounds, such as chloropropane, bromopropane, iodopropane, fluorobenzene, chlorobenzene, bromobenzene, iodobenzene, and chloropentafluorobenzene, were also tested, and the results are presented in Table 2. The sensor is more responsive to chlorinated than to brominated compounds, while it hardly responds to iodinated or fluorinated constituents.

TABLE 2

| | Relative Sensitivity to Homologous Halogenated Compounds | |
|---|---|---|
| Vapors | Concentration (ppm) | Response ($\times 10^{-6}$/ppm) |
| $C_3H_7Cl$ | 125 | 0.024 |
| $C_3H_7Br$ | 125 | 0.016 |
| $C_3H_7I$ | 125 | 0.003 |
| $C_6H_5F$ | 62.5 | 0.005 |
| $C_6H_5Cl$ | 62.5 | 0.029 |
| $C_6H_5Br$ | 62.5 | 0.020 |
| $C_6H_5I$ | 125 | 0.003 |
| $C_6ClF_5$ | 12.5 | 0.022 |

Figure 9:
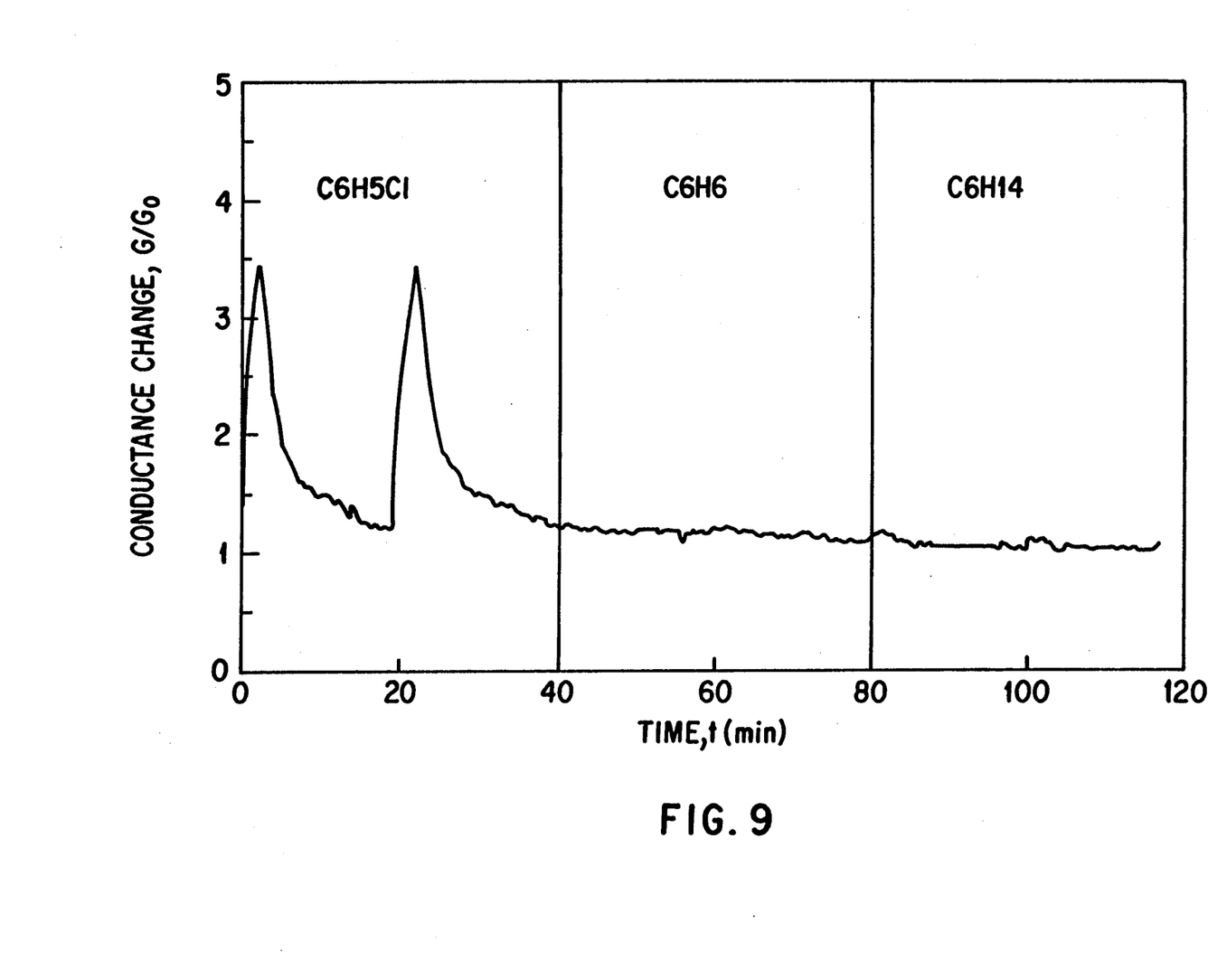
FIG. 9 illustrates the selectivity of the sensor to chlorobenzene and its nonresponsiveness to benzene or hexane.

FIG. 9 shows the selectivity of the chlorinated hydrocarbon sensor. The same sensor was exposed to the same concentration (100 ppmv) of three compounds— chlorobenzene, benzene, and hexane—was detected by the same sensor. There is a great difference in sensor response between chlorinated and chlorine-free hydrocarbons. The responses of the sensor to various chemical vapors and gases, $NO_2$, CO, $O_2$, are shown in Table 3. The sensor only responds to chlorinated hydrocarbons, and not to atmospheric gases or to hydrocarbon vapors.

TABLE 3

Relative Sensitivity of Halogenated Compounds Sensor

| Vapor or Gas | Concentration (ppm) | Response ($\times 10^{-6}$/ppm) |
| --- | --- | --- |
| $CHCl_3$ | 10 | 0.078 |
| $CH_3CCl_3$ | 10 | 0.071 |
| $C_6H_5Cl$ | 10 | 0.030 |
| $C_6H_6$ | 100 | ND* |
| $C_6H_{14}$ | 100 | ND |
| $NO_2$ | 50 | ND |
| CO | 334 | ND |
| $O_2$ | 100% | ND |

*ND - Not detectable (corresponds to a signal $1 \times 10^{-9}$)

The sensor yielded no significant response to 100 ppmv of $Cl_2$, but it elicited a strong response to <200 ppmv of HCl. Strong responses were also elicited by two simulants of chemical warfare agents—chloropentafluorobenzene. (0.022 micromhos/ppmv) and chloroethyl ethyl sulfide.

Figure 10:
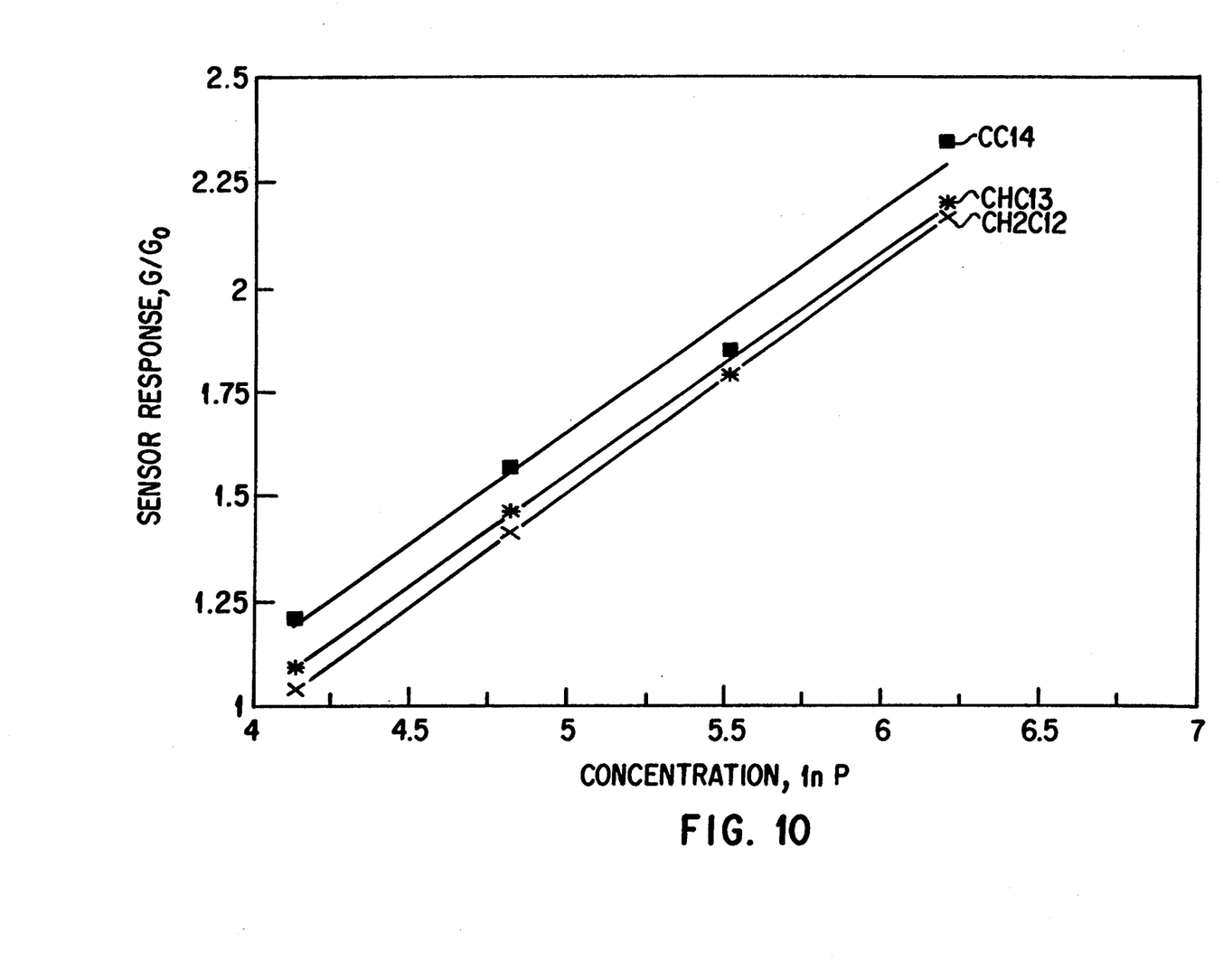
FIG. 10 shows the concentration dependencies of the sensor responses to $CCl_4$, $CHCl_3$, and $CH_2Cl_2$.

The effect of the degree of halogenation was tested by exposing the sensor to dichloromethane, chloroform, and carbon tetrachloride. The relationship between the logarithmic sensor conductance change and the logarithmic gas concentration is shown in FIG. 10. The conductance change upon exposure to chlorinated hydrocarbons increases in the order:

$CH_2Cl_2 < CHCl_3 < CCl_4$.

Figure 11:
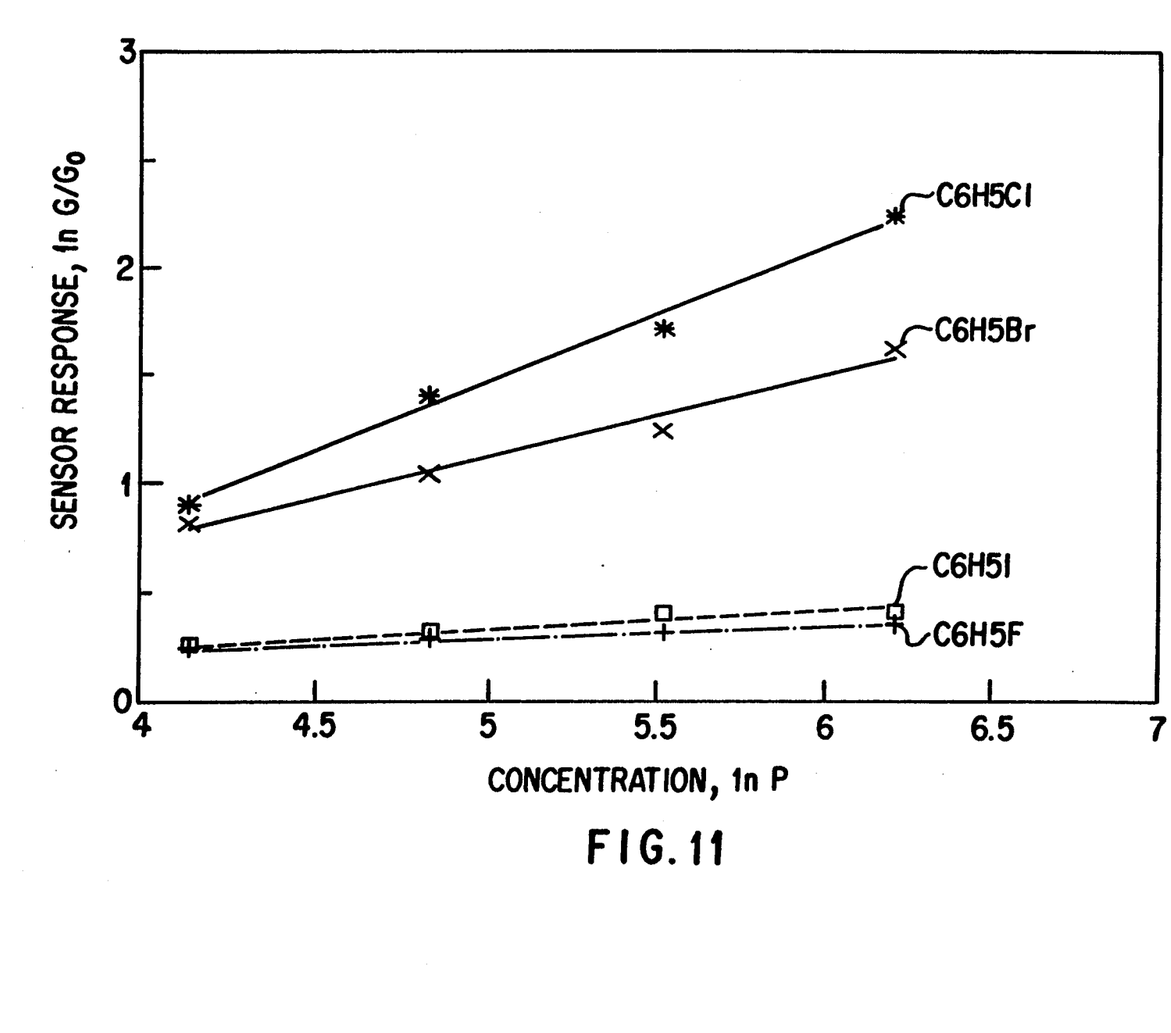
FIG. 11 shows the concentration dependencies of the sensor responses to chlorobenzene, bromobenzene, iodobenzene, and fluorobenzene.
Figure 12:
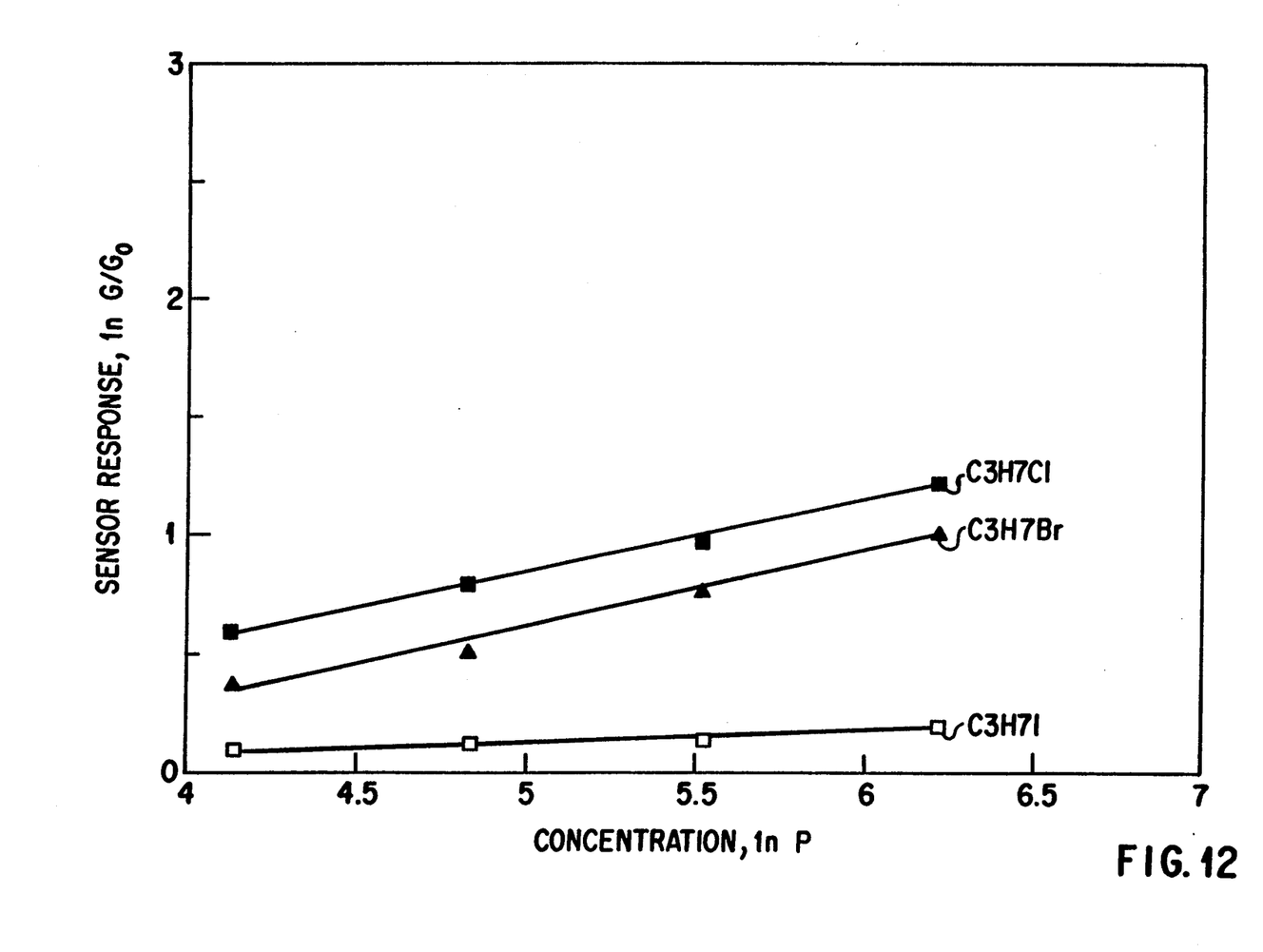
FIG. 12 shows the concentration dependencies of the sensor responses to chloropropane, bromopropane, and iodopropane.

Two sets of homologous halogenated compounds: (1) fluorobenzene, chlorobenzene, bromobenzene, and iodobenzene; and (2) chloropropane, bromopropane, and iodopropane, were individually tested over the concentration range of 62.5–500 ppmv. The test data, as given in FIGS. 11 and 12, show that the sensitivity of the sensor to the halogenated compounds follows the order:

R—Cl>R—Br>R—F and R—I, where R— is given organic radical.

Effect of Humidity

Figure 13:
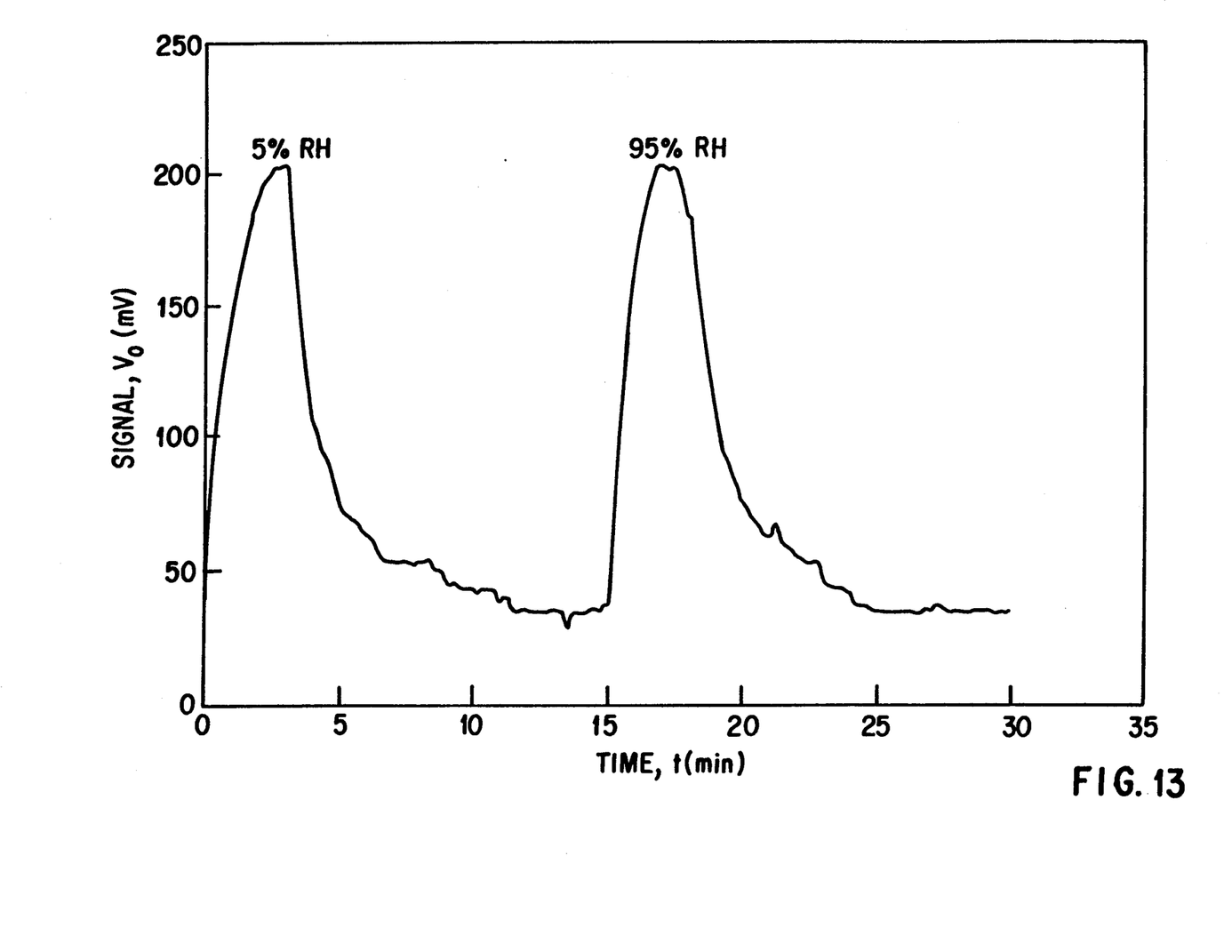
FIG. 13 shows the responses of the sensor to 100 ppmv of 1,1,1-trichloroethane at relative humidities of 5% and 95%.

The effect of humidity was determined by monitoring the sensor response to 100 ppmv of 1,1,1trichloroethane at the relative humidities of 5% and 95%. The results, as plotted in FIG. 13, shown no influence of humidity on the sensor signal.

Sensor Lifetime and Stability

A durability test demonstrated a sensor lifetime of over 20 days with continuous exposure to a concentration of 100 ppmv of chlorobenzene in air. The sensor response is stable over a given day, with variations of only about 10% of the signal, and is stable over the sensor lifetime, with a total variation in sensitivity of less than 50%. The lifetime appears to be a function of the concentration exposure history of the sensor.

In summary, the halogenated compounds sensor of this invention has a high sensitivity and selectivity, good precision and a reasonable lifetime. It can be used for the determination of chlorinated or brominated hydrocarbons or of HCl. Besides its obvious use as a selective sensor for the direct monitoring of halogenated compounds, it may also have possible application as a detector in gas chromatography. The sensor has been used to examine two chlorinated hydrocarbon vapors, chloroform and 1,1,1-trichloroethane at concentrations of 125–1000 ppbv. Lower levels may be possible with a higher gain amplifier. The sensor is completely insensitive to commonly occurring gases, such as CO, $O_2$ or $NO_2$ and to halogen-free hydrocarbon vapors, such as hexane and benzene. The sensor is quite stable over its entire lifetime and is not affected by humidity or by the presence of air.

There will now be obvious to those skilled in the art many modifications and variations of the aforedescribed embodiment which, however, shall remain within the scope of our invention if defined by the following claims.

We claim:

1. A sensor for detecting a halogenated compound in a gaseous mixture comprising two noble-metal electrodes in contact with and separated by a material whose effective electrical resistance decreases upon exposure to a halogenated compound, said material comprising sodium lanthanum fluoride silicate, having the chemical formula $NaLa_4(SiO_4)_3F$.

2. The sensor of claim 1, wherein said material is in the form of a bead in which said electrodes are at least partly embedded.

3. The sensor of claim 2, wherein one of said electrodes is in the form of a coil surrounding the embedded part of the other electrode.

4. The sensor of claim 3, wherein said electrodes comprise platinum.

5. The sensor of claim 3, comprising a means for heating the bead and maintaining it at a temperature in excess of 450° C.

6. The sensor of claim 5, wherein said heating means includes means for resistive heating of said coil.

7. Apparatus for the monitoring or detection of a halogenated compound in a gaseous mixture comprising:

a sensor whose effective electrical resistance decreases upon exposure to a halogenated compound, said sensor comprising sodium lanthanum fluoride silicate, having the chemical formula $NaLa_4(SiO_4)_3F$;

means for measuring said effective resistance; and means for maintaining said sensor at a temperature in excess of 450° C.

8. The sensor of claim 7, where said temperature is in the range of 500°–600° C.

9. Apparatus of claim 7, comprising two electrodes wherein at least part of an end of each said electrode is embedded in a bead of a material containing said sodium lanthanum fluoride silicate and separated by a gap comprising said material, said resistance-measuring means comprising means for applying a voltage between the two electrodes and measuring the electrical current through said electrodes.

10. Apparatus of claim 9, wherein one of said electrodes is in the form of a coil surrounding the embedded part of the other electrode, and wherein said temperature-maintaining means comprises means for resistive heating of said coil.

11. The apparatus of claim 10, wherein said other electrode is at a positive potential with respect to said coil, and said voltage is in excess of 1 volt.

12. The apparatus of claim 11, wherein said voltage is in the range of 1–5 volts.

13. The apparatus of claim 10, wherein said temperature-maintaining means comprises a circuit for automatically adjusting the electrical resistance of said coil.

14. The apparatus of claim 13, comprising a means for drawing a sample of gas that is to be monitored and flowing that sample over said material at a predetermined rate.

15. The apparatus of claim 14, comprising a microprocessor or microcomputer for controlling and processing signals from said resistance-measuring, temperature-maintaining, and sample-flowing means.

16. A method of manufacturing a sensor for detecting the presence of a halogenated compound comprising the steps of:

mounting two electrodes separated by a gap onto at least one electrically insulating support;

filling said gap with a paste comprising a mixture of lanthanum oxide, lanthanum fluoride, and sodium silicate; and sintering the paste at a temperature so as to at least partly convert said mixture to a sodium lanthanum fluoride silicate having the chemical formula $NaLa_4(SiO_4)_3F$.

17. The method of claim 16, wherein the molar ratios of the components of said mixture correspond to the chemical formula $La_2O_3.3Na_2SiO_3$.

18. The method of claim 17, comprising the steps of coating parts of said electrodes with said paste, drying the coated electrodes by heating, covering the electrodes with more paste so as to fill said gap, and gradually bringing the electrodes to a temperature at which sintering of the paste yields the $NaLa_4(SiO_4)_3F$ product.

19. The method of claim 19, wherein said sintering temperature is about 800° C.

20. The method of claim 19, wherein the duration of the sintering step is 3–8 hours.

* * * * *